(12) United States Patent
Murdeshwar et al.

(10) Patent No.: US 12,343,059 B2
(45) Date of Patent: Jul. 1, 2025

(54) STEAM ABLATION DEVICE FOR TREATMENT OF MENORRHAGIA

(71) Applicant: GYRUS ACMI, INC., Southborough, MA (US)

(72) Inventors: Nikhil M. Murdeshwar, Maple Grove, MN (US); Thomas J. Holman, Princeton, MN (US)

(73) Assignee: GYRUS ACMI, INC., Westborough, MA (US)

( * ) Notice: Subject to any disclaimer, the term of this patent is extended or adjusted under 35 U.S.C. 154(b) by 1192 days.

(21) Appl. No.: 17/096,043

(22) Filed: Nov. 12, 2020

(65) Prior Publication Data

US 2021/0153921 A1 May 27, 2021

Related U.S. Application Data (60) Provisional application No. 62/939,820, filed on Nov. 25, 2019.

(51) Int. Cl.
*A61B 18/18* (2006.01)
*A61B 18/04* (2006.01)
*A61B 18/00* (2006.01)

(52) U.S. Cl.
CPC .... *A61B 18/04* (2013.01); *A61B 2018/00095* (2013.01); *A61B 2018/00101* (2013.01);
(Continued)

(58) Field of Classification Search
CPC ..... A61B 18/04; A61B 18/08; A61B 18/1206; A61B 18/14; A61B 2018/00005;
(Continued)

(56) References Cited

U.S. PATENT DOCUMENTS 10,154,871 B2 * 12/2018 Sharkey .................. A61B 18/04
11,457,969 B2 * 10/2022 Hoey ...................... A61B 18/04
(Continued)

FOREIGN PATENT DOCUMENTS

CN 107847259 3/2018
CN 112826582 A 5/2021
(Continued)

OTHER PUBLICATIONS

"European Application Serial No. 20209736.6, Extended European Search Report mailed Apr. 12, 2021", 7 pgs.
(Continued)

*Primary Examiner* — Michael F Peffley
*Assistant Examiner* — Amanda L Zink
(74) *Attorney, Agent, or Firm* — Schwegman Lundberg & Woessner, P.A.

(57) ABSTRACT

Disclosed herein is a vapor therapy device for producing intra-uterine tissue effects. The device can include a shaft, including a proximal portion and a distal portion, a fluid-expandable medium, near the distal portion of the shaft, a fluid-delivery conduit, extending between the proximal portion and the distal portion of the shaft, the fluid-delivery conduit comprising an outlet, near the distal portion of the shaft, for delivery of the fluid toward the medium, and an in vivo heat generator, near the distal portion of the shaft, to heat the fluid. A method of treating a patient for menorrhagia with the device can include introducing a medium, in a contracted state, into a patient, delivering a fluid toward the medium to expand the medium in vivo; generating heat in vivo on or near the medium to vaporize the fluid, and exposing a treatment site to the vaporized fluid.

19 Claims, 8 Drawing Sheets

(52) U.S. Cl.
CPC ............... *A61B 2018/0022* (2013.01); *A61B 2018/00559* (2013.01); *A61B 2018/00577* (2013.01); *A61B 2018/048* (2013.01)

(58) Field of Classification Search
CPC ........... A61B 2018/00017; A61B 2018/00023; A61B 2018/00095; A61B 2018/00101; A61B 2018/0022; A61B 2018/00238; A61B 2018/00559; A61B 2018/00577; A61B 2018/00589; A61B 2018/00601; A61B 2018/00625; A61B 2018/00744; A61B 2018/00875; A61B 2018/044; A61B 2018/048; A61B 2018/1253; A61B 2018/126

See application file for complete search history.

(56) References Cited

U.S. PATENT DOCUMENTS

| | | | | |
|---|---|---|---|---|
| 11,672,584 | B2* | 6/2023 | Hoey | A61B 18/04 607/96 |
| 12,042,215 | B2* | 7/2024 | Govari | A61B 18/1492 |
| 2002/0019627 | A1* | 2/2002 | Maguire | A61B 18/1492 606/41 |
| 2002/0177846 | A1* | 11/2002 | Mulier | A61B 18/04 607/96 |
| 2004/0068306 | A1* | 4/2004 | Shadduck | A61B 18/04 607/96 |
| 2006/0135955 | A1* | 6/2006 | Shadduck | A61B 18/04 607/104 |
| 2006/0161233 | A1* | 7/2006 | Barry | A61N 7/022 607/113 |
| 2006/0224154 | A1* | 10/2006 | Shadduck | A61B 18/042 606/41 |
| 2008/0132826 | A1* | 6/2008 | Shadduck | A61B 18/04 604/114 |
| 2009/0054871 | A1* | 2/2009 | Sharkey | A61B 18/04 606/27 |
| 2009/0125010 | A1* | 5/2009 | Sharkey | A61B 18/04 606/27 |
| 2012/0245583 | A1* | 9/2012 | Truckai | A61B 18/042 606/41 |
| 2013/0030410 | A1 | 1/2013 | Drasler et al. | |
| 2015/0126990 | A1 | 5/2015 | Sharma et al. | |
| 2015/0335380 | A1 | 11/2015 | Chee et al. | |
| 2016/0051322 | A1* | 2/2016 | Asirvatham | A61N 1/0551 606/41 |

FOREIGN PATENT DOCUMENTS

| | | |
|---|---|---|
| EP | 3244820 A2 | 11/2017 |
| WO | WO-0000100 A1 | 1/2000 |

OTHER PUBLICATIONS

"European Application Serial No. 20209736.6, Response Filed Oct. 18, 2021 to Extended European Search Report mailed Apr. 12, 2021", 8 pgs.

"Chinese Application Serial No. 202011341437.3, Office Action mailed Feb. 27, 2025", w English translation, 21 pgs.

* cited by examiner

LAYER C

STEAM ABLATION DEVICE FOR TREATMENT OF MENORRHAGIA

CROSS-REFERENCE TO RELATED APPLICATION

This application claims the benefit of priority to U.S. Provisional Patent Application Ser. No. 62/939,820, filed Nov. 25, 2019, the contents of which are incorporated herein in their entirety.

BACKGROUND

Menorrhagia refers to menstrual bleeding lasting more than seven days at a time, and can often include heavy bleeding. Menorrhagia affects more than ten million American women every year, meaning about one out of every five women nationally has menorrhagia. Untreated menorrhagia can cause anemia, a common blood problem in which the patient lacks sufficient healthy red blood cells to carry adequate oxygen throughout the body.

Menorrhagia can be caused by uterine problems, hormonal problems, or other illnesses. Some particular causes can include, but are not limited to, growths or tumors in the uterus, cancer of the uterus or cervix, pregnancy-related problems such as miscarriage or ectopic pregnancy, bleeding disorders, some types of birth control, kidney, thyroid, or liver diseases, infection of the female reproduction organs such as pelvic inflammatory disease, menopause, child birth, fibroids or polyps in the lining or muscles of the uterus, taking certain drugs such as aspirin, or combinations thereof.

SUMMARY/OVERVIEW

A variety of approaches can be taken for treatment of menorrhagia. For example, menorrhagia can be treated by ablating endometrial tissue in the uterus so that the tissue does not continue to heavily bleed during the menstrual cycle. Such treatment can be referred to as global endometrial ablation (GEA). GEA approaches can use a variety of ablation technologies to ablate the endometrium and prevent menorrhagia. Some of these approaches can include radiofrequency (RF) energy, microwave energy, cryogenics, thermal energy, steam, and plasma ablation technologies. Devices and methods for delivery of these approaches can be large and can create patient pain or discomfort when used. Approaches involving generating of steam outside the patient can induce a risk of leaking steam to areas other than the endometrial tissue.

To help increase efficacy, and reduce complications, the present disclosure, among other things, describes an in vivo vaporization approach to endometrial ablation. Such an approach can include providing or using a vapor therapy device for producing intra-uterine tissue effects. The vapor therapy device can include a portion that can be sized and shaped for at least partial insertion into a patient. The device can have a shaft, including a proximal portion and a distal portion. The device can further include a fluid-expandable medium at or near the distal portion of the shaft, a fluid-delivery conduit extending between the proximal portion and the distal portion of the shaft with an outlet near the distal portion of the shaft, such as for delivery of the fluid toward the medium, and an in vivo heat generator, near the distal portion of the shaft, to heat the fluid, such as for in vivo vaporization.

This document also describes a method of treating menorrhagia in a patient. The method can include introducing a medium, such as in a contracted state, into a patient, delivering a fluid toward the medium to expand the medium in vivo, generating heat in vivo on or near the medium such as to vaporize the fluid, and such that a treatment site can be exposed to the vaporized fluid.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure describes, among other things, an apparatus and method of treating menorrhagia (heavy menstrual bleeding) with an ablation device configured to generate steam or other vapor in vivo, such as directly inside the uterus. The device can include an electrical cable and thin fluid delivery pipe that deliver fluid and electrical energy toward a sponge-like media. The media can be collapsed upon entry into the uterus, allowing easier access with less pain, and can expand upon exposure to fluid in vivo. Heat can then be generated in vivo to produce vapor in the uterus.

The device can provide for creation of steam or other gas phase vapor in vivo, directly inside the uterus. This can help inhibit or prevent leaking of vapor outside the desired treatment area. The media can help produce more uniform distribution of vapor and may help prevent leaking of vapor into the vagina as might otherwise occur if an external vapor source were used. Additionally, the device can be, in some cases, battery-operated and in some cases, portable.

Figure 1A:
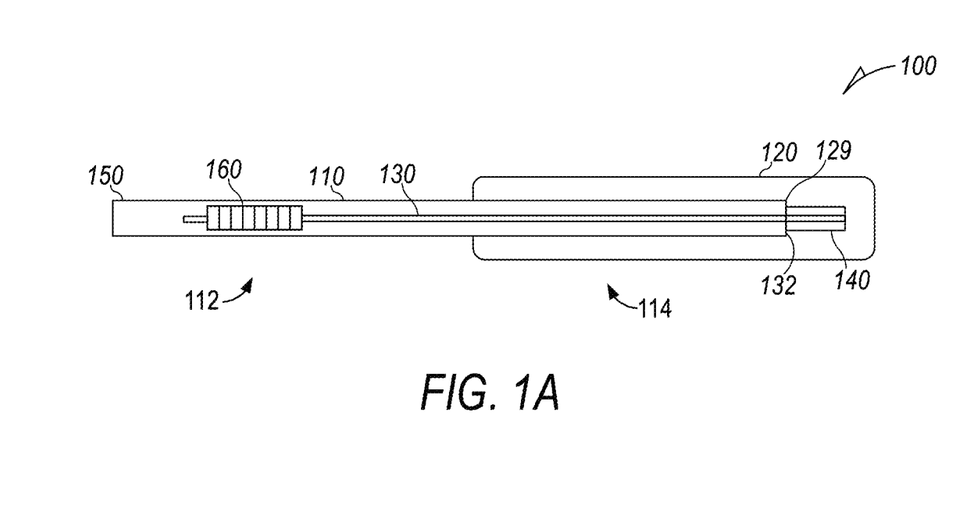
FIGS. 1A-1B illustrate schematic diagrams of an example of a vapor therapy device for producing intra-uterine tissue effects for treating menorrhagia.
Figure 1B:
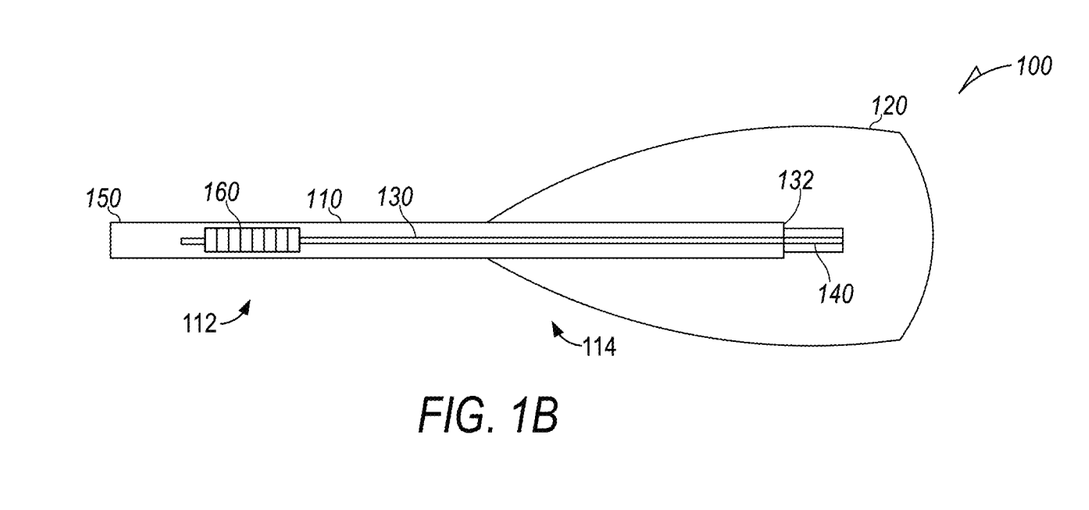

FIGS. 1A-1B illustrate schematic diagrams of a portion of an example of a device 100 with a portion sized and shaped for insertion into a patient. FIG. 1A shows a device 100 in a lower profile state. FIG. 1B shows the device 100 in a higher profile state. FIGS. 1A-1B will be discussed together. The device 100 can include a shaft 110 with a proximal portion 112 and a distal portion 114, a fluid-expandable medium 120, a fluid-delivery conduit 130 with an outlet 132, an in vivo heat generator 140, a hand piece 150, and a fluid source 160.

The device 100 can include, for example, a vapor therapy device such as for producing one or more intra-uterine tissue effects, such as ablation of endometrial tissue with an in vivo generated vapor such as steam. In the device 100, the shaft 110 can extend from a proximal portion 112 to a distal portion 114. The fluid-expandable medium 120 can be located at or near the distal portion 114 of the shaft 110. The hand piece 150 can be mounted or connected to the proximal portion 112 of the shaft 110. The fluid-delivery conduit 130 can run within or along the shaft 110, such as from the proximal portion 112 to the distal portion 114, with the outlet 132 located in or near the fluid-expandable medium 120. The fluid source 160 can be connected to the fluid-delivery conduit 130 at the proximal end 112. The in vivo heat generator 140 can be located on or near distal end 114, terminating in or near the fluid-expandable medium 120. The in vivo heat generator 140 can be connected through an electrical conductor running from the proximal end 112 to the distal end 114.

The shaft 110 with the proximal portion 112 and the distal portion 114 can be sized, shaped, or arranged for partial insertion of the device 100 into a patient. The shaft 110 can include a composite or metallic material. The shaft 110 can have a diameter of less than about 6 mm. The proximal portion 112 can be near an operator when the device 100 is in use. The distal portion 114 can be sized, shaped, or arranged for insertion into the patient.

The fluid-expandable medium 120 can include, for example, a sponge-like material that can absorb and retain a liquid or fluid such as water. For example, a sponge-like material can include fibrous material made of polymer, metals (such as silver), or combinations thereof. In an example, the fluid-expandable medium 120 can be elastic and inflatable, such as using a balloon-type material. The fluid-expandable medium 120 can be permeable to vapor. In some cases, the fluid-expandable medium 120 can have a porosity that allows for vapor generation, when expanded. The fluid-expandable medium 120 can, for example, withstand temperature of up to about 130° C.

The fluid-expandable medium 120 can have both a lower profile state and a relatively higher profile state. In the lower profile state, the fluid-expandable medium can be, for example, collapsed on shaft 110. In the lower profile state, the fluid-expandable medium can be, for example, narrower in profile, such as for easier insertion into a patient. In the lower profile state, the fluid-expandable medium 120 can have a lateral profile outer dimension, such as a diameter, of less than about 6 mm, such as for easier transcervical insertion into the patient.

In the higher profile state, the fluid-expandable medium 120 can be expanded to a larger size, such as a larger diameter, cross-section, or volume, such as while within the uterus. When in the relatively higher profile state, the fluid-expandable medium 120 can have a lateral profile outer dimension, such as a diameter, of about 3 cm to about 4 cm.

The fluid-expandable medium 120 can include, for example, a urethane material. In some cases, the fluid-expandable medium 120 can include more than one layer of material, such as discussed below with reference to FIG. 2.

The fluid-delivery conduit 130 can deliver fluid to the fluid-expandable medium 120 at or via the outlet 132. When deployed, the fluid-expandable medium 120 can cover or encase the outlet 132 so that the fluid can be delivered directly into the fluid-expandable medium 120. The fluid can include, for example, water, saline, or other liquid suitable for vaporization in vivo.

In some cases, the outlet 132 can include a valve 129 in fluid communication with the fluid-delivery conduit 130. The valve 129 can be configured to be user-controlled to allow or prevent or otherwise control delivery of the fluid towards the fluid-expandable medium 120 via the valve 129. The operator can trigger the valve 129, for example, by a button or trigger on hand piece 150. In some cases, the operator can trigger the valve 129 by a foot pedal or other actuator coupled to the device 100.

Fluid can be provided to the fluid-expandable medium 120 via the fluid-delivery conduit 130 from the fluid source 160. In an example, the fluid source 160 can include a pre-filled syringe such as can be integrated with or attached to the hand piece 150. The syringe can have, for example, a plunger, such as can be actuated by a coiled spring, or can be manually actuated by the operator. The fluid source 160 can include a tube, hose, pump, or combination thereof, such as for connecting the device 100 to a larger canister, container, faucet, or other reservoir holding the fluid. The fluid can include, for example, water, saline, or one or more other types of vaporizable fluids useable for vapor ablation.

In some cases, the fluid source 160 can be user-actuated by a trigger, button, foot pedal, or other actuator coupled to a valve 129 or other flow regulator associated with the fluid source. In some cases, the fluid source 160 can be automatically actuated, for example, such as when a threshold electrical impedance level is reached in the fluid-expandable medium 120. Impedance level can be sensed, for example, by electrodes such as can be provided at the distal end 114 of the device 100, or by the in vivo heat generator 140. Electrical impedance can drop when the fluid-expandable medium 120 is wet. This can, for example, trigger actuation of the fluid source 160, For example, where the fluid source 160 includes a syringe, a threshold impedance reading be used as a sensed indication such as can induce the syringe spring and insertion of the fluid into the fluid-delivery conduit 130 towards the fluid-expandable medium 120. Various example control systems and logic for adjustment of fluid delivery based on impedance of the fluid-expandable medium 120 is shown in FIGS. 1C-1F.

Figure 1C:
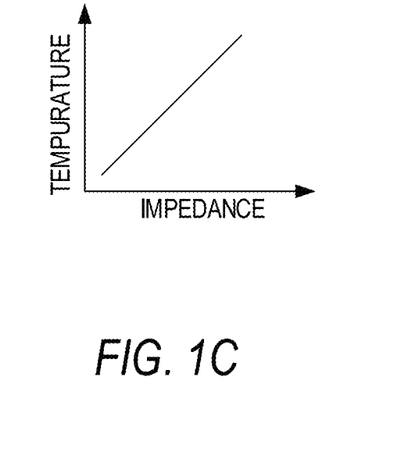
FIGS. 1C-1D illustrate graphs showing thermal feedback, impedance, and saturation levels of tissue treated with a vapor therapy device.
Figure 1D:
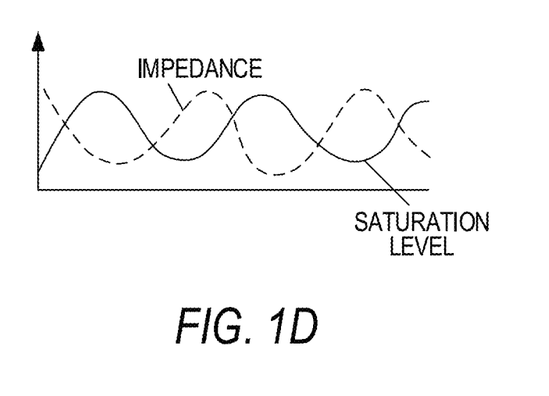

FIGS. 1C-1D illustrate graphs showing thermal feedback, impedance, and saturation levels of tissue treated with a vapor therapy device. In some examples, temperature of the system can continuously increase in proportion to impedance (FIG. 1C). In some examples, impedance and saturation level of the target tissue can varying relative each other (FIG. 1D). For example, the moistness level (e.g., saturation with vapor) of the medium can be inversely proportional to the electrical impedance of that medium. In one example, a high impedance can indicate a dry medium.

Figure 1E:
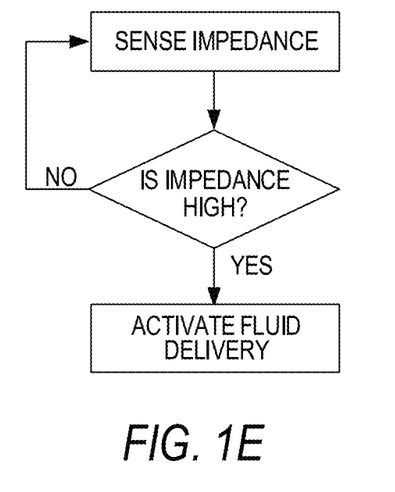
FIGS. 1E-1F illustrate flow charts showing application of vapor therapy for intra-uterine tissue effects.

FIGS. 1E-1F illustrate flow charts showing application of vapor therapy for intra-uterine tissue effects. FIG. 1E shows an example method of altering fluid delivery. In FIG. 1E, the method includes sensing an impedance of the fluid expandable medium, such as by running an electrical current through the medium. The sensed impedance can be compared, for example, to a regular or average impedance for that type of medium. If the impedance is relatively high, this could indicate the fluid-expandable medium is dry. In this case, the system can initiate delivery of fluid to the medium. If the impedance is low, indicating the fluid-expandable medium is wet, the system may not initiate delivery of fluid.

Figure 1F:
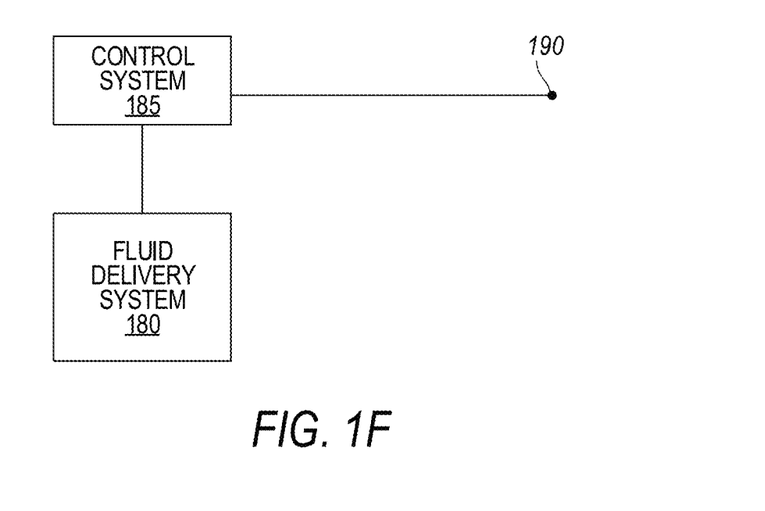

Similarly, FIG. 1F depicts a control system for delivery of fluid to the fluid-expandable medium. In FIG. 1F, the fluid delivery system 180, such as a pump, or injector syringe as discussed above, can be in communication with the control system 185. The control system 185 can receive signals sensed by the impedance sensor 190, which can be in or near the fluid-expandable medium. Based on the sense signal, the control system 185 can output a signal to fluid delivery system 180 to initiate or cease delivery of fluid to the fluid-expandable medium.

The fluid-expandable medium 120 can partially or fully sheath the in vivo heat generator 140. In some cases, in vivo heat generator 140 can be fully enclosed by the fluid-expandable medium 120 so that the in vivo heat generator 140 can provide heat directly inside the fluid-expandable medium 120. When dry (e.g., in the lower profile state), the fluid-expandable medium 120 can be compressed along or around the in vivo heat generator 140, such as for insertion into the patient. The fluid-expandable medium 120 can be expanded by filling with the fluid, or in some cases can be user-actuated to expand.

The in vivo heat generator 140 can be configured to vaporize the fluid from the fluid-delivery conduit 130 in vivo. The in vivo heat generator 140 can heat the fluid exiting the fluid-delivery conduit 130 at the outlet 132 as it exits the fluid-delivery conduit 130, or after the fluid has moved out of the fluid-delivery conduit 130, into the fluid-expandable medium 120, and expanded the fluid-expandable medium 120. In some cases, the in vivo heat generator 140 can heat the fluid when the fluid-delivery conduit 130 is partially expanded. The in vivo heat generator 140 can stimulate vaporization of the fluid, such as by producing heat by providing electrical or electromagnetic energy such as can help induce a phase change in that fluid. In some cases, the phase change can be from liquid to gas. In some cases, a mist or aerosol, such as wet steam, can be produced, where liquid droplets are present. Where steam is produced, the saturation of water droplets in the steam can vary depending on the desired ablation effect. The amount of heat produced by the in vivo heat generator 140 can vary depending on the fluid used, the specific capacity of that fluid, and the energy required to vaporize that fluid.

The in vivo heat generator 140 can produce, for example, electromagnetic energy such as radiofrequency (RF) energy, microwave energy, infrared (IR) energy, visible light energy, ultraviolet (UV) energy, or other appropriate types of energy for vaporizing liquid in the fluid-expandable medium 120.

The in vivo heat generator 140 can include, for example, a bipolar or monopolar electrode for delivery of electromagnetic energy. Both bipolar and monopolar electrodes can make use of high frequency electrical current to cut, coagulate, desiccate, or fulgurate tissue. With a monopolar electrode, the current can pass from the probe of the electrode (e.g., in vivo heat generator 140) to the target tissue and through the patient to a return pad to complete the electrical circuit. In contrast, with a bipolar electrode, current passes through the tissue between two arms of a forceps type electrode.

In some cases, the in vivo heat generator 140 can be configured to produce heat by passing a current through a resistor. In some examples, the in vivo heat generator 140 can include an electrical wire, or other electrical conductor, running through the fluid-expandable medium 120, terminating in a resistive element for heat generator. In this case, the in vivo heat generator 140 can include, for example, nichrome, stainless steel or other appropriate resistive metallic material.

The hand piece 150, which can be sized, shaped, or arranged for operator use and holding, can be attached to proximal portion 112 of shaft 110. The hand piece 150 can include one or more triggers or buttons for initiating delivery of the fluid to the fluid-expandable medium 120, for initiating production of electromagnetic energy from the in vivo heat generator to vaporize that fluid, or both.

In some cases, the operator can use the device 100, for example, by inserting the distal portion 112 with the fluid-expandable medium 120 in a lower profile state (e.g., compacted) into the uterus of the patient, through the cervix. The operator can determine the correct placement of the device 100 in the patient, in some cases, by visual confirmation, through a scope (such as an endoscope) or camera integrated into the device. In some cases, the operator can use other imaging technology such as ultrasound. In other examples, where the operator intends to have the fluid-expandable medium 120 touch, extend, or distend the uterine wall, the operator can physically detect when the device 100 touches the uterine wall.

After insertion, the operator can actuate the fluid source so that the fluid can be delivered down the fluid-delivery conduit 130 and dripped, sprayed, or poured into the fluid-expandable medium 120, causing the fluid-expandable medium 120 to swell with the liquid from a lower profile state (e.g., compacted) to a higher profile state (e.g., expanded), and partially or wholly filled with fluid. Subsequently or simultaneously, the user can activate the in vivo heat generator 140 to produce electromagnetic energy in or near fluid-expandable medium 120. In some cases, the fluid can be heated as it runs down the fluid-delivery conduit 130.

The produced electromagnetic energy can induce vaporization of the fluid, such as production of a gas or steam. The vapor can be produced and self-contained in utero, preventing leakage of vapor outside the uterus, and prevent leakage through the cervix. This can, for example, protect other organs and tissue outside the uterus. The produced vapor can ablate the endometrium. Ablation can include, for example, removal or destruction of the target tissue by the application of high heat vapor. In some cases, ablation can cause tissue necrosis. The target tissue can scar in response to ablation, preventing it from copious bleeding and producing menorrhagia effects. When the vapor is absorbed by the endometrium, the vapor can lose latent heat and convert to fluid. This can affect penetration of the vapor into the endometrium layer, and modify the effects of ablation to prevent ablation of tissue beyond a desired depth.

Figure 2:
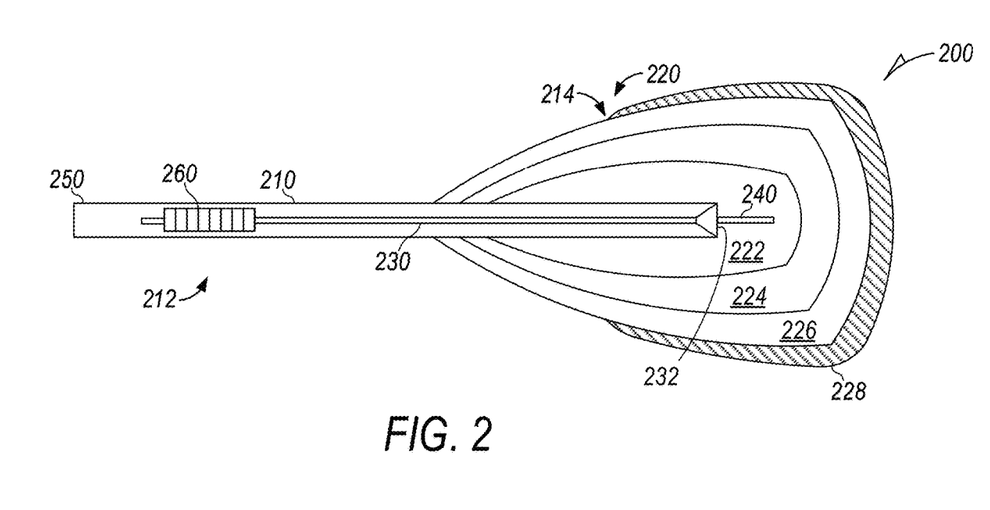
FIG. 2 illustrates a schematic diagram of an example of a vapor therapy for treating menorrhagia, the device having a medium with multiple layers.

FIG. 2 illustrates a schematic diagram of a portion of an example device 200 for insertion into a patient. The components of the device 200 are similar to, and connected in the same way, as the corresponding components of the device 100, except where otherwise noted. The device 200 can include a shaft 210 with a proximal portion 212 and a distal portion 214, a fluid-expandable medium 220, a fluid-delivery conduit 230 with an outlet 232, an in vivo heat generator 240, a hand piece 250, and a fluid source 260.

In the device 200, the fluid-expandable medium 220 can include several layers, for example, the fluid-expandable medium 220 can include a pressure barrier layer 222, a transport layer 224, a tissue compliant layer 226, and an optional cover layer 228.

The pressure barrier layer 222 can be, for example, an internal layer closer to the in vivo heat generator within the device 200. In some cases, the pressure barrier layer 222 can partially or fully encompass the outlet 232 of the fluid-delivery conduit 230 so that fluid delivered to the fluid-expandable medium 220 first arrives at the pressure barrier layer 222. Similarly, the transport layer 224 can partially or fully encompass the pressure barrier layer 222. In some examples, the transport layer 224 can include more than one stratum of material.

The tissue compliant layer 226 can partially or fully encompass the transport layer 224. The optional cover layer 228 can partially or fully encompass the tissue compliant layer 226, so that the cover layer 228 is closest to the endometrium when the device 200 is inserted into a patient's uterus.

The pressure barrier layer 222 can, for example, maintain a pressure threshold that can prevent premature expansion of the fluid-expandable medium 220 when the fluid source 260 begins to move the fluid into the fluid-expandable medium 220. Once the pressure threshold is reached by fluid being inserted towards the fluid-expandable medium 220, the fluid can expand the fluid-expandable medium 220 to a relatively higher profile state, where the fluid can cause expansion of the fluid-expandable medium 220 through the transport layer 224 and the tissue compliant layer 226.

In some cases, the transport layer 224 can include one or more stratum situated in a middle portion of the fluid-expandable medium 220. The transport layer 224 can be configured to convey the fluid from the fluid source 260 through the pressure barrier layer 222 out to the tissue compliant layer 226.

The tissue compliant layer 226 can be, in some cases, an outer layer of fluid-expandable medium 220. The tissue compliant layer 226 can be made of a material that interacts well with the target tissue, without causing damage to the target tissue. In some cases, when the fluid-expandable medium 220 is in a higher profile state, the tissue compliant layer 226 can touch or directly interact with the target tissue. In some cases, where the tissue compliant layer 226 touches the target tissue, the fluid-expandable medium can extend or distend the uterine wall.

Each of the layers 222, 224, 226, 228, of the fluid-expandable medium 220 can be made of, for example, urethane, or other types of fluid-expandable material. When the fluid-expandable medium 220 is in a lower profile state (e.g., compacted for insertion into a patient uterus), all of the layers 222, 224, 226, 228, together can have a diameter of less than about Comm. When in a higher profile state (e.g., filled with fluid and expanded inside a patient uterus), all of the layers of the fluid-expandable medium 220 together can have a diameter of about 3 cm to about 4 cm, inclusive. When in the higher profile state, the fluid-expandable medium 220 can sometimes contact the side of the uterus, or sometimes distend the side of the uterus.

In some cases, the transport layer can 224 have a porosity greater than the pressure barrier layer 222, and the tissue compliant layer 226 can have a porosity greater than the transport layer 224, so that the porosity of the fluid-expandable medium 220 increases from the pressure barrier layer 222 towards the tissue compliant layer 226. Example porosity ranges can be seen below in Table 1.

TABLE 1

Example porosity of fluid-expandable medium layers.

| Layer | Shore A Durometer | Porosity |
|---|---|---|
| Pressure barrier layer 222 | 75D | 10% |
| Transport layer 224 | 55D | 50% |
| Tissue compliant layer 226 | 35D | 90% |
| Optional cover layer 228 | N/A | >90% |

Table 1 additionally shows an example hardness measure of each of the layers 222, 224, 226, 228. The example hardness, as measured by a Shore A Durometer, can, for example, indicate a greater resistance to indentation corresponding to how hard the material, such as a polymer, elastomer, or rubber, is. In an example, the pressure barrier layer 222 can have a higher hardness, of about 75D on the Shore durometer scale, compared to about 55D for the transport layer 224 and about 35D for the tissue compliant layer 226. A gradient of hardness, going from more hard to less hard moving from the internal layers to the external layers, can provide for controlled release of vapor from the fluid-expandable medium 220. Thus, the layers 224, 226, may expand more fully and more quickly than the pressure barrier layer 222, when filled with the fluid, situating more of the fluid for conversion to vapor nearer the more external portions of the fluid-expandable medium 220.

In Table 1, example porosity ranges for the layers 222, 224, 226, 228, are given. The example porosity of the pressure barrier layer 222 can be less, e.g., about 10% compared to the transport layer 224, which can have a porosity of about 50%, and less than the porosity of the tissue compliant layer 226, which can be about 90%. A gradient of porosity in the multi-layer fluid-expandable medium 220 can allow for controlled dispersion of the fluid throughout the fluid-expandable medium 220, and controlled dispersion of vapor when that fluid is heated by the in vivo heat generator 240. For example, the vapor can travel more quickly through the more external, more porous layers.

In some cases, the transport layer 224 can have a higher heat capacity than the pressure barrier layer 222, and the tissue compliant layer 226 can have a higher heat capacity than the transport layer 224. Thus, the heat capacity of fluid-expandable medium 220 can increase from the pressure barrier layer 222 to the tissue compliant layer 226.

A gradient of heat capacity in the multi-layer fluid-expandable medium 220 can allow for controlled heating of the fluid-expandable medium 220 when vapor ablation is desired. As the electromagnetic energy produced by the in vivo heat generator 240 travels outward towards the endometrium, the heat transfer can be slowed so as to produce vapor and ablate the tissue at a specific rate.

The optional cover layer 228 can be included in some examples of device 200. The optional cover layer 228 can include a continuous layer or one or more sections on various parts of the fluid-expandable medium 220 in which more efficient transfer of heat is desired, such as when coordinating the fluid-expandable medium 220 to one or more areas of tissue inside a patient uterus. The cover layer 228 can include, for example, a thermally conductive material, and allow for more efficient transfer of heat and vapor through the fluid-expandable medium 220 to the endometrium layer for ablation.

When fully expanded (such as in a relatively higher profile state), the fluid-expandable medium 220 can, in some cases, touch or distend the uterine wall. When in use, in some cases, the fluid-expandable medium can be held at constant temperature and pressure, such as above 120° C. In some cases, the in vivo heat generator can produce constant heat, while fluid could be provided at a constant pressure, as discussed in more detail with reference to FIG. 6. In some examples, pulsating temperature, pressure, or both, can be used, as discussed below with reference to FIG. 6. The various layers 222, 224, 226, 228, can allow for the operator to manipulate the timing of vapor delivery to the target tissue, and potentially deliver the vapor to various physical portions of the uterine wall.

Figure 3:
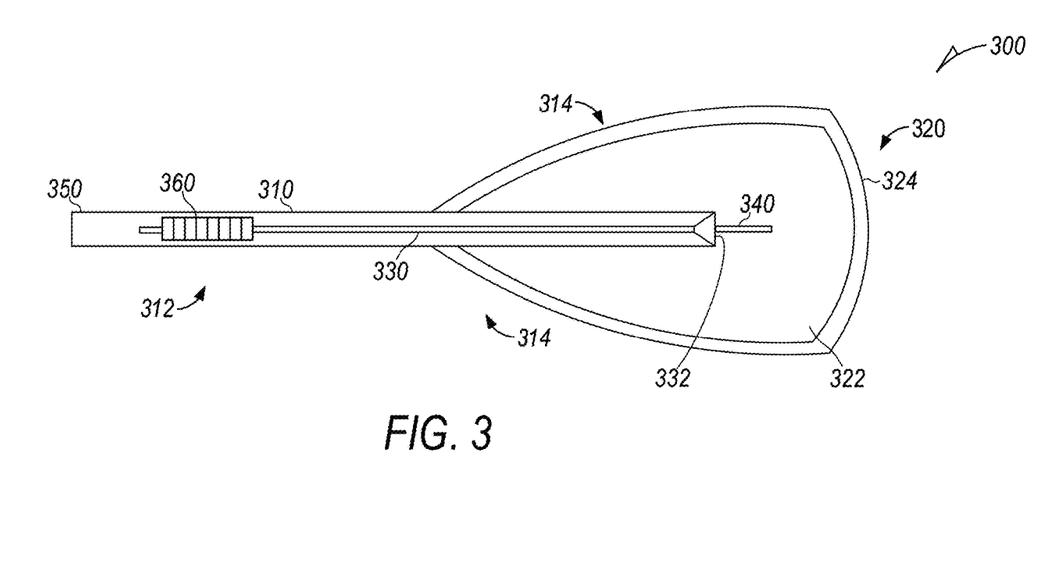
FIG. 3 illustrates a schematic diagram of an example of a vapor therapy device for treating menorrhagia, the device for providing superheated steam.

FIG. 3 illustrates a schematic diagram of a portion of an example device 300 for insertion into a patient. The components of the device 300 are similar to, and connected in the same way, as the corresponding components of the device 200, except where otherwise noted. The device 300 can include a shaft 310 with a proximal portion 312 and a distal portion 314, a fluid-expandable medium 320, a fluid-delivery conduit 330 with an outlet 332, an in vivo heat generator 340, a hand piece 350, and a fluid source 360.

The fluid-expandable medium 320 can be superheated with vapor during use. The fluid expandable medium 320 can include two layers, a gas transfer medium 322 and a cover layer 324. The gas transfer medium 322 can include, for example, a thermal transfer medium surrounding in vivo heat generator 340. The gas transfer medium 322 can have, for example, a specific capacity allowing slow transfer of heat.

The cover layer 324 can include, for example, a thermally conductive material. In some cases, cover layer 324 can include one or more stratum of urethane. The cover layer 324 can have a specific capacity suitable for storing heat. Storing of heat in cover layer 324 when fluid-expandable medium is expanded can allow for the temperature of nearby target tissue to increase or maintain heat during ablation.

The gas transfer medium 322 can allow for collection of fluid in the fluid-expandable medium 320. Upon heating and vaporization of that fluid, the fluid-expandable medium 320 gas transfer layer 322 is super saturated with vapor. This can occur, for example, where the fluid-expandable medium 320 is heated by the in vivo heat generator 340 to about 100° C. or above.

Figure 4:
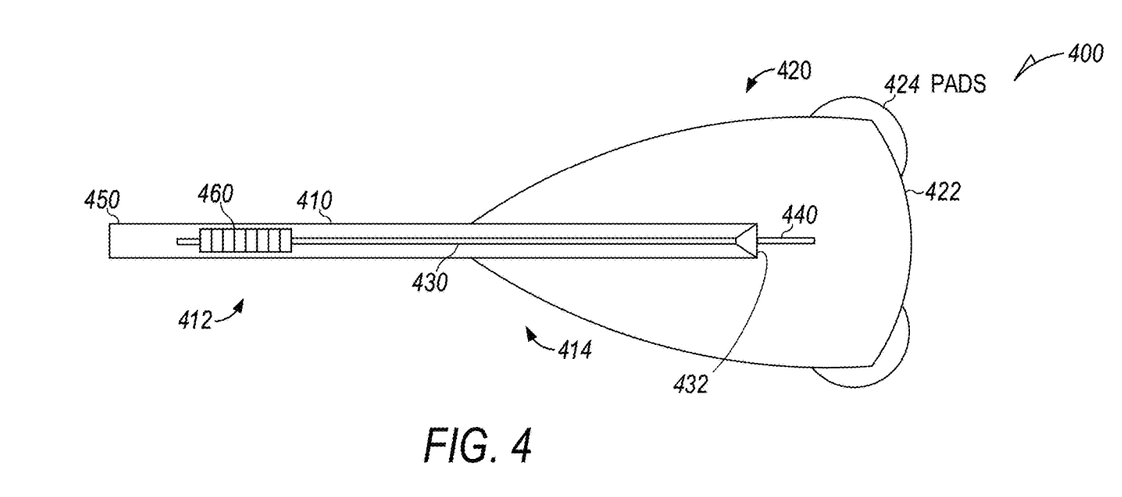
FIG. 4 illustrates a schematic diagram of an example of a vapor therapy device for treating menorrhagia, the device including thermally insulating pads.

FIG. 4 illustrates a schematic diagram of a portion of an example device 400 for insertion into a patient. The components of the device 400 are similar to, and connected in the same way, as the corresponding components of the device 100, except where otherwise noted. The device 400 can include a shaft 410 with a proximal portion 412 and a distal portion 414, a fluid-expandable medium 420, a fluid-delivery conduit 430 with an outlet 432, an in vivo heat generator 440, a hand piece 450, and a fluid source 460.

In the device 400, the fluid-expandable medium 420 can include a main layer 422 and pads 424. The main layer 422 can include, for example, urethane or other expandable material that can be filled with fluid. The pads 424 can be thermally insulating, and prevent transfer of heat and vapor out of the fluid-expandable medium at the portions on or near the pads 424. The pads 424 can be made of a material, for example, that is more compliant than urethane so that the pads can distend more as the fluid-expandable medium 420 is filled.

The pads 424 can be situated so that, for example, they cover the openings of the fallopian tubes in a patient when the fluid-expandable medium 420 is inserted into the uterus and in the fluid-expandable medium 420 enters a higher profile (e.g., expanded) state. This could potentially protect the fallopian tubes and their entrances, discouraging vapor from travelling up the fallopian tubes and effecting or ablating tissue outside of the endometrium. The pads 424 can, in some cases, be made of a very compliant materials so that pads push into and partially seal off the entrances to the fallopian tubes.

Figure 5:
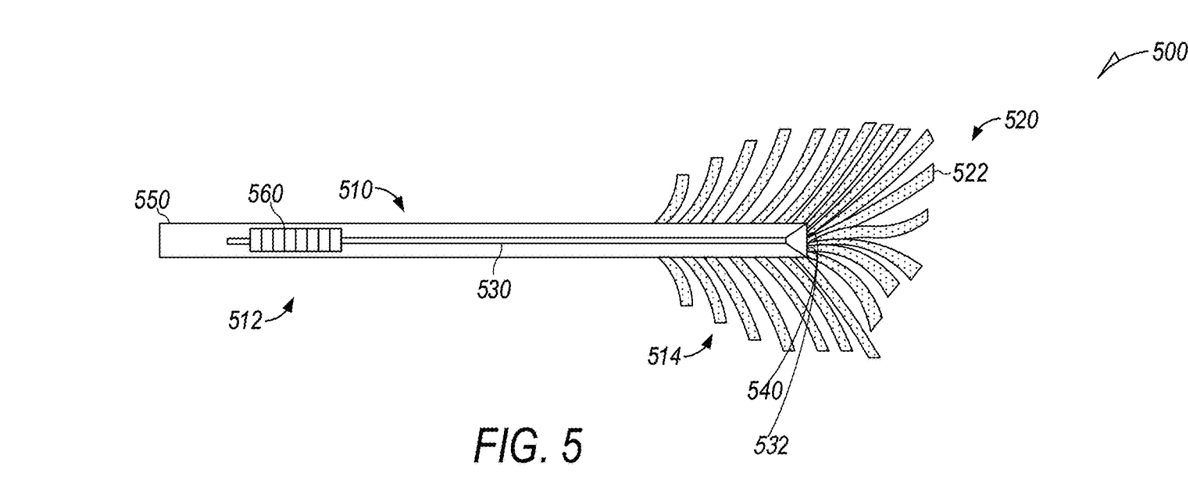
FIG. 5 illustrates a schematic diagram of an example of a vapor therapy device for treating menorrhagia, the device including capillary tubes.

FIG. 5 illustrates a schematic diagram of a portion of an example device 500 for insertion into a patient. The components of the device 500 are similar to, and connected in the same way, as the corresponding components of the device 100, except where otherwise noted. The device 500 can include a shaft 510 with a proximal portion 512 and a distal portion 514, a fluid-expandable medium 520, a fluid-delivery conduit 530 with an outlet 532, an in vivo heat generator 540, a hand piece 550, and a fluid source 560.

The fluid-expandable medium 520 can include capillary tubes 522 instead of multiple layers of expandable material. The capillary tubes 522 can, for example, extend outward from the shaft 510 when filled with fluid from the fluid source 560. The capillary tubes 522 can be made of a low durometer material, such as a material with low hardness so that the capillary tubes 522 are pliant when the device 500 is inserted into a patient uterus. The capillary tubes 522 can each have holes for expulsion of steam evenly throughout the uterus.

Figure 6A:
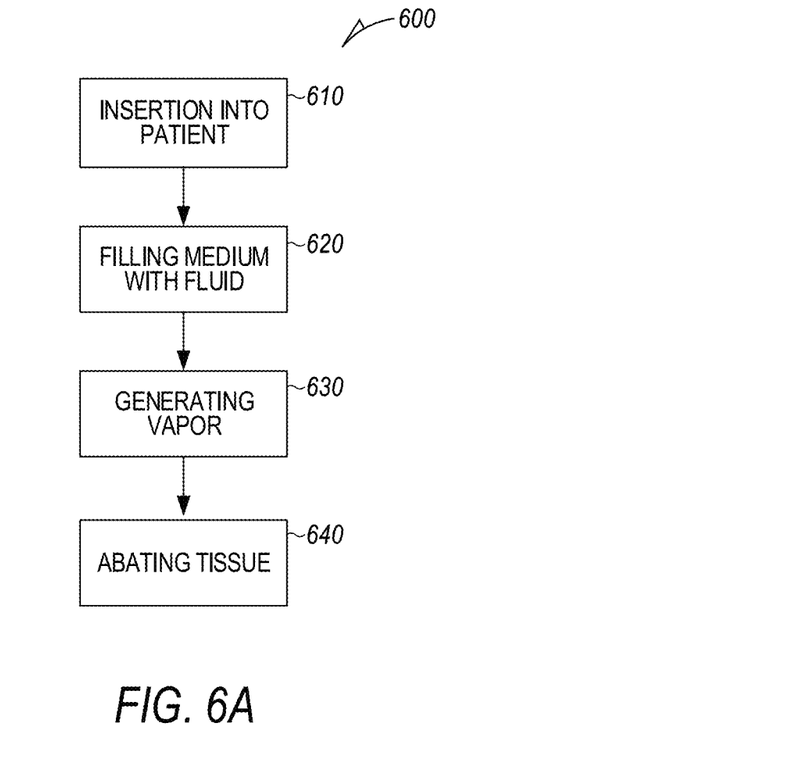
FIG. 6A illustrates a flow chart of a method of treating menorrhagia with a vapor therapy device.

FIG. 6A illustrates a flow chart of method 600 of treating a patient with an ablation device. The method 600 can include inserting the device into the uterus of a patient (610), supplying fluid to a fluid-expandable medium on the device (620), and exiting an in vivo heat generator with electromagnetic energy to produce vapor (630) and ablating the target tissue on the uterine surface.

First, in step 610, the operator can insert the device into the patient's uterus. The operator can insert the distal end of the device into the patient in a transcervical manner without other incision or entry point. In this step, the device's fluid-expandable medium can be in a low profile or contracted state, so that the diameter of a cross-section of the distal end of the device entering the patient is less than about 6 mm. This can, for example, allow for more efficient transcervical insertion with less patient pain.

Subsequently, in step 620 the operator can begin directly fluid towards the fluid-expandable medium in vivo, though, for example, a pump, tube, drip line, or other source of fluid. In some cases, the fluid can be directed into the medium through use of a fluid delivery conduit embedded in the shaft of the device, and attached to an outside source of the fluid. In some cases, the device can be directly attached to a fluid line or faucet. The operator can, in some cases, adjust the flow rate or pressure of the fluid before or during the procedure. The fluid can include, for example, water, saline, or other fluid as appropriate to expand the medium. The fluid can optionally include lidocaine.

As the medium is filled with fluid, it can expand to a higher profile state in the uterus. The medium can be partially filled with the fluid, saturated with the fluid, or superheated with the fluid. The medium can be filled, for example, as it expands. The medium can expand so that it is centered in and near the uterine lining, so that it is touching the uterine lining, or so that it distends the uterine lining. The rate of expansion of the medium can be tailored based on the rate of introduction of fluid and the specific materials of the medium itself. In some cases, the medium can have multiple layers with specific porosities, affecting the rate of fluid movement within the medium.

In step 630, the operator can induce generation of electromagnetic energy to vaporize the fluid in the medium. The user can generate electromagnetic energy with an in vivo heat generator located on or near the shaft of the device near the distal end, for example, embedded inside the fluid-expandable medium. The heat generator can include, for example, a resistive wire, or a mono or bipolar electrode. The electromagnetic energy produced can be, but is not limited to, radiofrequency (RF) energy, or other appropriate types of energy for vaporizing fluid in the medium. In some cases, the in vivo heat generator can be switchably connected via an electrical conductor to an electromagnetic energy source, such as to electrosurgical generator (ESG) circuitry configured to provide suitable electromagnetic energy.

The energy generated can heat the fluid in the medium such that it induces a phase change, and the fluid is vaporized. The heat generation can occur on or near the medium to vaporize the fluid. In some cases, heat generation and vaporization of the fluid can be done after the medium is fully saturated with the fluid. In that case, the fluid would disperse throughout and fully extend the medium to its higher profile state prior to vaporization. In some cases, the heat generation and vaporization can be done simultaneously with delivery of fluid to the medium. In that case, the fluid can be pumped into the medium as the heat generator is used to vaporize the fluid. This can sometimes mean vaporization can occur while the medium is being expanded, if that is desired.

Figure 6B:
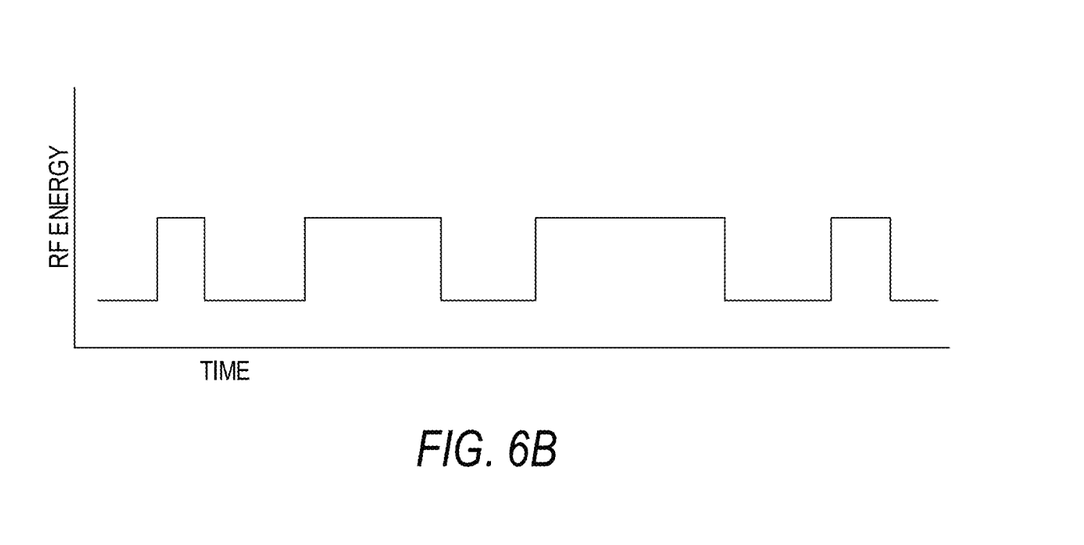
FIGS. 6B-6F illustrate schematic graphs depicting properties of various vapor therapy devices for treating menorrhagia.

Heat generation can be done at a constant rate, or in pulses. If heat generation is done in a pulsatile fashion, it can be duty cycled as shown in FIG. 6B. The types and amounts of materials included in fluid-expandable medium can affect how quickly and efficiently the tissue is treated with vapor.

Figure 6C:
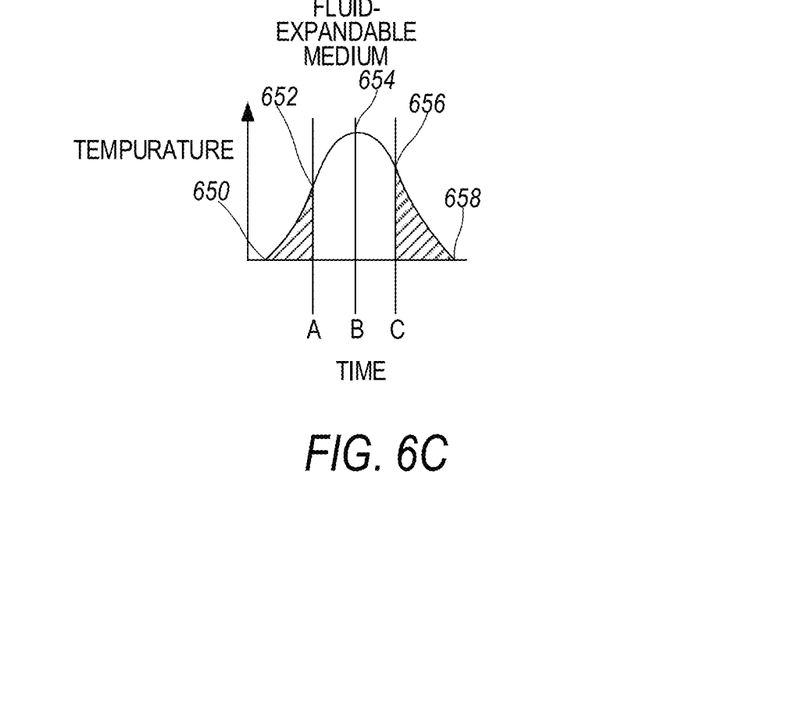

For example, where a fluid-expanded medium with three layers is used, the layers can have a constant temperature drop profile. An example tissue temperature versus time curve over the course of treatment is shown in FIG. 6C where a balloon-type device is used. In FIG. 6C, the example device can have layer A, B, and C, such as a pressure barrier layer, a transport layer, and a tissue compliant layer, respectively, as discussed with reference to FIG. 2 above. In FIG. 6C, the temperature of the tissue can increase as the device inflates through layer A (e.g., a pressure barrier layer). Over the course of treatment shown in FIG. 6C, the balloon can expand between layers A and C on the graph.

In FIG. 6C, the initial temperature (650) of the incoming fluid increases as the fluid passes into layer A and is heated to a vapor (652). The temperature of the now-vapor continues to increase as it approaches layer B (654), then drops as it reaches layer C (656), at which point the vapor can contact the tissue. The temperature of the vapor can continue to drop as the tissue is treated with the vapor (658).

Figure 6D:
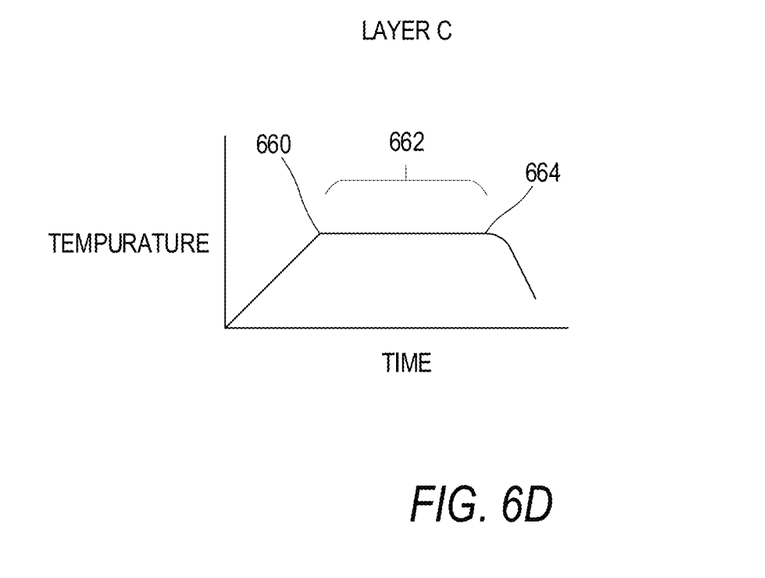
Figure 6E:
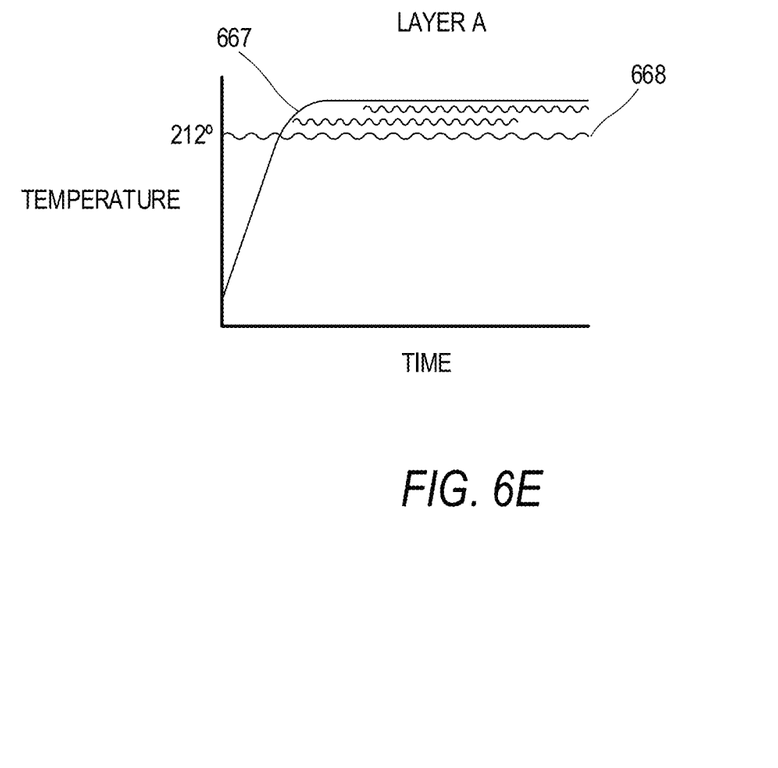
Figure 6F:
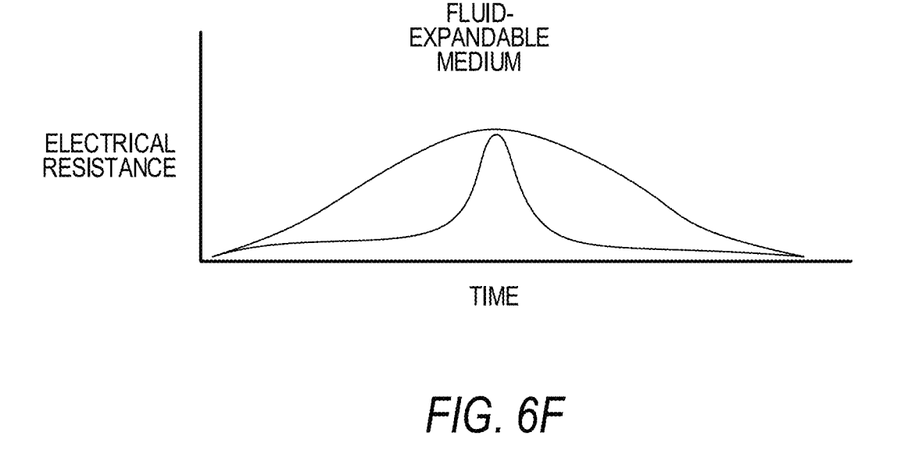

FIGS. 6D and 6E shown temperature curve data for individual layers of the example three-layer fluid-expandable medium. 6D shows the temperature during treatment of layer C, the tissue compliant layer. Initially, the layer C reaches the temperature of the steam (660) from internal layer A. The temperature of layer C can, for example, plateau during ablation (662) at the temperature of the tissue (664), By contrast, the temperature of layer A (667), the pressure barrier layer, once heated can stay higher than the tissue temperature (668) throughout the procedure as shown in FIG. 6E. FIG. 6F depicts the electrical resistance of the fluid-expandable medium over the course of a procedure for ablation.

As depicted in FIGS. 6C-6F, wherein heated vapor is moving out of the medium and towards the targeted treatment site, the layers can create a consistent temperature drop in the vapor so that by the time the vapor reaches the targeted tissue, it is the desired temperature for ablation. For example, a layer A closest to the shaft of the device can have about a 10% temperature drop as the medium is heated. The second layer B, an intermediate layer partially encompassing layer A, can have about a 30% temperature drop, and a third layer C, or an outer layer closest the tissue, can have about a 50% temperature drop. This effect can be created by using materials with varying heat capacities. Such a constant temperature drop could potentially allow for ablation of the tissue without damage.

Additionally, in some cases, the fluid-expandable medium can include a more thermally conductive region that is more distal, and a less thermally conductive region. This can allow for higher temperature vapor to approach certain portions of target tissue, while other regions receive lower temperature vapor. In some cases, the fluid-expandable medium can include reduced thermal conductivity portions configured to be located toward fallopian tubes in the patient as discussed in reference to FIG. 4 above.

In another example, pulsating heat can be used. As explained further herein, where a fluid-expanded medium with three layers is used (see, e.g., FIG. 2), the layers can each have pulsatile temperature profiles. In this case, a first layer D could be located nearest the shaft of the device, and have a temperature drop of no more than about 50%. A second layer E, an intermediate layer, could have a temperature drop of no more than about 30%. A third layer F, nearest the target tissue, could have a temperature drop of no more than about 10%.

Where the heat is pulsatile, the flow of heat and vapor treatment can be duty cycled. In this case, the temperature of the vapor when it reaches layer A would be the highest temperature of the steam, with a small amount of heat being lost as the vapor travelled through layers B and C towards the target tissue. This could allow, for example, for the operator to manipulate the temperature of the steam so that is was about 212 F when hitting the target tissue.

Subsequently, in step 640, the treatment site can be exposed to the vapor at a high temperature for ablation. The treatment site can include, for example, tissue in the endometrium causes menorrhagia. The treatment site tissue can be, for example, saturated or superheated with the vapor, so that the vapor effects the tissue deep enough to cause ablation, but not so deep that other layers of tissue are harmed.

Finally, the operator can turn off the device and remove it from the patient. The time of treatment can be, for example, about 1 to 2 minutes total for vapor ablation of the uterine lining.

The proposed device and methods discussed herein allow for delivery of steam to ablate endometrial tissue with a lower risk of generating or leaking steam outside the uterus, such as into the vagina. Additionally, the device itself is small and less bulky, as the electrical cable and thin liquid delivery lumen can be included in a narrow shaft for delivery.

Various Notes & Examples

Each of these non-limiting examples can stand on its own, or can be combined in various permutations or combinations with one or more of the other examples.

Example 1 can include a vapor therapy device for producing intra-uterine tissue effects, for at least partial insertion into a patient, the device comprising: a shaft, including a proximal portion and a distal portion, a fluid-expandable medium, near the distal portion of the shaft, a fluid-delivery conduit, extending between the proximal portion and the distal portion of the shaft, the fluid-delivery conduit comprising an outlet, near the distal portion of the shaft, for delivery of the fluid toward the medium, and an in vivo heat generator, near the distal portion of the shaft, to heat the fluid.

Example 2 can include Example 1, wherein the in vivo heat generator is configured to vaporize the fluid in vivo.

Example 3 can include any of Examples 1-2, further comprising a valve in fluid communication with the fluid-delivery conduit, wherein the valve is configured to be user-controlled to control delivery of the fluid towards the medium via the valve.

Example 4 can include any of Examples 1-3, wherein the fluid-expandable medium is permeable to vapor.

Example 5 can include any of Examples 1-4, wherein the fluid-expandable medium has a porosity that increases when expanded.

Example 6 can include any of Examples 1-5, wherein the fluid-expandable medium includes a balloon.

Example 7 can include any of Examples 1-6, wherein the fluid-expandable medium includes a sponge.

Example 8 can include any of Examples 1-7, wherein the fluid-expandable medium includes a relatively compressed state for insertion into the patient and is capable of expanding to a relatively expanded state.

Example 9 can include any of Examples 1-8, wherein the relatively compressed state includes a diameter of less than about 6 mm for insertion.

Example 10 can include any of Examples 1-9, wherein the relatively expanded state includes a diameter of about 6 cm to about 9 cm when expanded.

Example 11 can include any of Examples 1-10, wherein the fluid-expandable medium includes: a pressure barrier layer encompassing the outlet of the fluid-delivery conduit, a transport layer at least partially encompassing the pressure barrier layer, and a tissue compliant layer at least partially surrounding the transport layer.

Example 12 can include any of Examples 1-11, wherein the transport layer has a porosity greater than the pressure barrier layer and wherein the tissue compliant layer has a porosity greater than the transport layer.

Example 13 can include any of Examples 1-12, wherein the transport layer has a higher heat capacity than the pressure barrier layer, and wherein the tissue compliant layer has a higher heat capacity than the transport layer.

Example 14 can include any of Examples 1-13, wherein the fluid-expandable medium includes a more thermally conductive region that is more distal to the outlet than a less thermally conductive region of the fluid-expandable medium.

Example 15 can include any of Examples 1-14, wherein the fluid-expandable medium includes reduced thermal conductivity portions configured to be located toward respective fallopian tubes in the patient.

Example 16 can include any of Examples 1-15, wherein the in vivo heat generator is configured to produce heat by passing a current through a resistor.

Example 17 can include a method of treating a patient comprising introducing a medium, in a contracted state, into a patient, delivering a fluid toward the medium to expand the medium in vivo, generating heat in vivo on or near the medium to vaporize the fluid, and exposing a treatment site to the vaporized fluid.

Example 18 can include Example 17, wherein delivering a fluid into the medium expands the medium such that the medium contacts the treatment site.

Example 19 can include any of Examples 17-18, wherein delivering a fluid into the medium expands the medium such that the medium distends the treatment site.

Example 20 can include any of Examples 17-19, wherein generating heat on or near the medium is done after delivering the fluid into the medium such that the fluid first disperses in the medium and is then vaporized in the medium.

Example 21 can include any of Examples 17-20, wherein generating heat on or near the medium is done concurrently with delivering the fluid into the medium such that the fluid is vaporized as it disperses in the medium.

Example 22 can include any of Examples 17-21, wherein generating heat is done at a constant rate.

Example 23 can include any of Examples 17-22, wherein generating heat is done in pulses.

Example 24 can include any of Examples 17-23, wherein exposing the treatment site includes saturating the treatment site with the vaporized fluid.

Example 25 can include any of Examples 17-24, wherein exposing the treatment site includes superheating the treatment site with the vaporized fluid. Example 26 can include any of Examples 17-25, wherein exposing the treatment site includes exposing the treatment site to the heated medium.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A vapor therapy device for producing intra-uterine tissue effect, for at least partial insertion into a patient, the device comprising:
   a shaft, including a proximal portion and a distal portion;
   an in vivo heat generator, near the distal portion of the shaft;
   a fluid-expandable medium, near the distal portion of the shaft, and fully sheathing the in vivo heat generator, wherein the fluid-expandable medium comprises:
      a pressure barrier layer encompassing an outlet of a fluid-delivery conduit;
      a transport layer at least partially encompassing the pressure barrier layer; and
      a tissue compliant layer at least partially surrounding the transport layer;
   the fluid-delivery conduit, extending between the proximal portion and the distal portion of the shaft, the fluid-delivery conduit comprising the outlet, near the distal portion of the shaft, for providing fluid into the fluid-expandable medium, wherein the in vivo heat generator is configured to heat the fluid inside the fluid-expandable medium.

2. The device of claim 1, wherein the in vivo heat generator is configured to vaporize the fluid in vivo.

3. The device of claim 1, further comprising a valve in fluid communication with the fluid-delivery conduit, wherein the valve is configured to be user-controlled to control delivery of the fluid towards the medium via the valve.

4. The device of claim 1, wherein the fluid-expandable medium is permeable to vapor.

5. The device of claim 1, wherein the fluid-expandable medium has a porosity that increases when expanded.

6. The device of claim 1, wherein the fluid-expandable medium comprises a balloon.

7. The device of claim 1, wherein the fluid-expandable medium comprises a sponge.

8. The device of claim 1, wherein the fluid-expandable medium comprises a relatively compressed state for insertion into the patient and is capable of expanding to a relatively expanded state.

9. The device of claim 8, wherein the relatively compressed state comprises a diameter of less than about 6 mm for insertion.

10. The device of claim 8, wherein the relatively expanded state comprises a diameter of about 6 cm to about 9 cm when expanded.

11. The device of claim 1, wherein the transport layer has a porosity greater than the pressure barrier layer and wherein the tissue compliant layer has a porosity greater than the transport layer.

12. The device of claim 1, wherein the transport layer has a higher heat capacity than the pressure barrier layer, and wherein the tissue compliant layer has a higher heat capacity than the transport layer.

13. The device of claim 1, wherein the fluid-expandable medium includes a more thermally conductive region that is more distal to the outlet than a less thermally conductive region of the fluid-expandable medium.

14. The device of claim 1, wherein the fluid-expandable medium includes reduced thermal conductivity portions configured to be located toward respective fallopian tubes in the patient.

15. The device of claim 1, wherein the in vivo heat generator is configured to produce heat by passing a current through a resistor.

16. The device of claim 1, wherein the outlet is located in the fluid-expandable medium.

17. The device of claim 1, wherein the pressure barrier layer maintains a pressure threshold to prevent premature expansion of the fluid-expandable medium when the fluid is provided into the fluid-expandable medium.

18. The device of claim 1, wherein the pressure layer, the transport layer, and the tissue compliant layer comprise a hardness measure indicating greater resistance to indentation.

19. The device of claim 18, wherein the hardness measure increases from the pressure layer toward the tissue compliant layer.

* * * * *